United States Patent
Wakabayashi et al.

(10) Patent No.: US 11,006,893 B2
(45) Date of Patent: May 18, 2021

(54) RECORDING PAPER USED FOR MEDICAL APPARATUS AND METHOD FOR PERFORMING PRINTING ON RECORDING PAPER

(71) Applicant: ATOM MEDICAL CORPORATION, Tokyo (JP)

(72) Inventors: Keisuke Wakabayashi, Saitama (JP); Kazunari Oowada, Saitama (JP); Yoshinori Asari, Saitama (JP); Ichiro Matsubara, Tokyo (JP)

(73) Assignee: ATOM MEDICAL CORPORATION, Tokyo (JP)

( * ) Notice: Subject to any disclaimer, the term of this patent is extended or adjusted under 35 U.S.C. 154(b) by 0 days.

(21) Appl. No.: 16/613,195

(22) PCT Filed: May 9, 2018

(86) PCT No.: PCT/JP2018/017919
§ 371 (c)(1),
(2) Date: Nov. 13, 2019

(87) PCT Pub. No.: WO2018/216468
PCT Pub. Date: Nov. 29, 2018

(65) Prior Publication Data
US 2020/0170563 A1    Jun. 4, 2020

(30) Foreign Application Priority Data

May 25, 2017  (JP) .............................. JP2017-103701

(51) Int. Cl.
*B41J 2/32*    (2006.01)
*G06K 9/18*    (2006.01)
(Continued)

(52) U.S. Cl.
CPC ............... *A61B 5/4362* (2013.01); *B41J 2/32* (2013.01); *C09D 11/50* (2013.01); *G06K 9/18* (2013.01); *G06K 9/2063* (2013.01)

(58) Field of Classification Search
CPC .......... B41J 2/315; B41J 2/32; B41M 5/0041; B41M 5/0052; B41M 5/0076;
(Continued)

(56) References Cited

U.S. PATENT DOCUMENTS

2002/0033853 A1    3/2002  Aratsu
2014/0265103 A1    9/2014  Sone et al.

FOREIGN PATENT DOCUMENTS

JP    2001-225519    8/2001
JP    2001-322329    11/2001
(Continued)

OTHER PUBLICATIONS

Extended European Search Report in Europe Application No. 18806131.1, dated Feb. 4, 2021, 10 pages.
(Continued)

*Primary Examiner* — Kristal Feggins
(74) *Attorney, Agent, or Firm* — Brinks Gilson & Lione (57) ABSTRACT

Provided is a method for performing printing on a recording paper with a medical apparatus that continuously prints acquired biological information of a patient on the recording paper while feeding the recording paper. The method includes reading a first identification image attached to the recording paper; determining whether or not the recording paper is a genuine product on the basis of a comparison result between information based on the read first identification image and paper information previously stored in the medical apparatus; reading a second identification image attached to the recording paper, and determining whether or not the recording paper is within an expiration date on the
(Continued)

basis of expiration date information included in information based on the read second identification image; and printing the biological information on the recording paper in a case where the recording paper is determined to be the genuine product and the recording paper is determined to be within the expiration date.

7 Claims, 4 Drawing Sheets

(51) Int. Cl.
*A61B 5/00* (2006.01)
*C09D 11/50* (2014.01)
*G06K 9/20* (2006.01)

(58) Field of Classification Search
CPC ..... B41M 5/0082; B41M 5/0094; A61B 5/00; G06K 9/2063; G06K 9/18
See application file for complete search history.

(56) References Cited

FOREIGN PATENT DOCUMENTS

| | | |
|---|---|---|
| JP | 2004-034313 | 2/2004 |
| JP | 2005-178093 | 7/2005 |
| JP | 2006-223335 | 8/2006 |
| JP | 2008-109955 | 5/2008 |
| JP | 2013-216054 | 10/2013 |
| JP | 2014-128943 | 7/2014 |
| JP | 2014-176916 | 9/2014 |

OTHER PUBLICATIONS

Stephen Enfield: "Thermal Paper storage and shelf life—how does your receipt last" dated Jul. 2, 2013, Retrieved from the Internet at URL: <https://web.archive.org/web/20150112004212/https://patch.com/massachusetts/danvers/thermal-paper—storage-and-shelf-life—how-long-does-your-receipt-last>, retrieved on Jan. 22, 2021, 8 pages.

RECORDING PAPER USED FOR MEDICAL APPARATUS AND METHOD FOR PERFORMING PRINTING ON RECORDING PAPER

This application is a 371 application of PCT/JP2018/017919 having an international filing date of May 9, 2018, which claims priority to JP2017-103701 filed May 25, 2017, the entire content of each of which is incorporated herein by reference.

TECHNICAL FIELD

The present invention relates to a recording paper used for medical apparatus, such as a fetal and maternal monitor used in the medical field, and a method for performing printing on the recording paper.

BACKGROUND ART

In the related art, there is known a fetal and maternal monitor used to monitor labor pain (uterine contraction) and fetal heart rate of a mother's body under pregnancy and delivery in medical facilities and to check the health (well-being) of a fetus (refer to Patent Literature 1). In recording paper on which biological information, such as fetal heart rate and labor pain intensity, is recorded by the fetal and maternal monitor, a legal storage duty period is set.

The fetal and maternal monitor according to Patent Literature 1 includes fetal heart rate calculation means for calculating the fetal heart rate from signals relating to fetus heartbeats detected by fetal heart rate detecting means, labor pain intensity calculation means for calculating the labor pain intensity from signals related to the labor pain intensity of a mother's body detected by the labor pain intensity detecting means, display means for displaying the fetal heart rate and the labor pain intensity, and recording means for outputting the fetal heart rate and the labor pain intensity to the recording paper. Accordingly, each of the fetal heart rate and the labor pain intensity is recorded over time on the display means and the recording paper. Then, as a doctor, a maternity nurse, and the like decipher the recording paper on which the fetal heart rate and the labor pain intensity are recorded, the doctor and the like can perceive the health condition of a fetus under pregnancy and delivery.

CITATION LIST

Patent Literature

Patent Literature 1: JP-A-2006-223335

SUMMARY OF INVENTION

Technical Problem

The recording means of the fetal and maternal monitor according to Patent Literature 1 is of a thermal array type. The recording paper used for a thermal array type printer is thermal recording paper constituted by thermal paper. In the thermal recording paper, genuine products manufactured so as to be suitable for the apparatus have high quality, the printing quality thereof is high, and the degradation thereof is also slow. However, many counterfeit products have low quality, the printing quality thereof is low, and the degradation thereof occurs easily. For example, in a case where a counterfeit product is used, yellowing and blurring may occur as well as the biological information (the contents of printing) of a patient, such as the fetal heart rate and the labor pain intensity, may be lost before a legal storage period expires. Additionally, in a case where the type and amount of medicine used for the thermal recording paper are not optimal to a heat generating element of the printer of the fetal and maternal monitor, use of a counterfeit product may lead to degradation and failure of the heat generating element.

If the thermal paper is stored over a long period of time, the thermal paper turns yellow or the printing state thereof deteriorates. Thus, the expiration date (use-by date) is set. The expiration date of the thermal recording paper can be determined as a user views an outer casing on which a lot number and the expiration date are written. However, if the thermal recording paper is mounted on the fetal and maternal monitor, the entire thermal paper cannot be viewed (neither the lot number nor the expiration date can be checked). Thus, the expiration date cannot be determined. For this reason, in printing the biological information having a legal storage period the biological information (the fetal heart rate, the labor pain intensity, and the like) of a patient may be printed on the thermal recording paper that has passed the expiration date and has deteriorated.

If the thermal recording paper that has passed the expiration date and has deteriorated is used, the quality of the printing may deteriorate and be blurred or the yellowing may occur, so that printing results may be lost earlier than expected. However, in a case where the biological information recorded on the recording paper is the fetal heart rate and the labor pain intensity, these kinds of information are not allowed to be lost before the expiration of the legal storage period.

For this reason, it is possible to perform discrimination between high-quality recording paper (genuine product) manufactured so as to be suitable for the fetal and maternal monitor (medical apparatus) and a counterfeit product that may cause problems, and the use-by date of the recording paper can be checked. Accordingly, it is desired to prevent loss of printed letters of the biological information, such as the fetal heart rate and the labor pain intensity (a method for performing printing on the recording paper in which the loss of the printed letters or the like can be suppressed, and the recording paper).

The invention has been made in view of such circumstances, and an object of the invention is to provide a recording paper and a printing method that can prevent loss of printed letters, or the like, in a medical apparatus, such as a fetal and maternal monitor.

Solution to Problem

A method for performing printing on a recording paper with a medical apparatus of the invention is a method for printing a recording paper with a medical apparatus that continuously prints acquired biological information of a patient on the recording paper while feeding the recording paper. The method includes reading a first identification image attached to the recording paper; determining whether or not the recording paper is a genuine product on the basis of a comparison result between information based on the read first identification image and paper information previously stored in the medical apparatus; reading a second identification image attached to the recording paper, and determining whether or not the recording paper is within an expiration date on the basis of expiration date information included in information based on the read second identification image; and printing the biological information on the recording paper in a case where the recording paper is determined to be the genuine product and the recording paper is determined to be within the expiration date. Here, the "genuine product" means a product manufactured so as to be suitable for printing by a predetermined medical apparatus.

In the invention, in a case where no proper first identification image and second identification image are detected, that is, in a case where the recording paper is not a genuine product, or in a case where the expiration date passes, the biological information is not printed on the recording paper even if the biological information of the patient is acquired. According to this, the printing of the biological information to the recording paper on which printed letters may be lost within a predetermined period is prevented. Thus, as well as the loss of the printed letters of the biological information of the patient can be prevented, the occurrence of yellowing or blurring can be prevented.

Additionally, in a case where a user mounts recording paper other than the genuine product on the medical apparatus or mounts recording paper, which is the genuine product and has passed the expiration date, on the medical apparatus, the biological information is not printed. Thus, the user can be urged to use the genuine product within the expiration date.

Moreover, if a logo mark with which a manufacturing company or a sales company for the recording paper, a manufacturing company or a sales company for the medical apparatus has received trademark registration is used as the first identification image, manufacturing of the recording paper with the first identification image by those other than a trademark owner can be suppressed, and counterfeit product damage can be effectively suppressed.

In the method for performing printing to a recording paper with a medical apparatus of the invention, the second identification image may be read only in a case where the recording paper is determined to be a genuine product by using the first identification image.

In the invention, the determination of the genuine product based on the first identification image is previously performed. Thus, in a case where the recording paper is determined not to be a genuine product, reading of the second identification image becomes unnecessary. According to this, even if the determination processing based on the second identification image is not executed, printing to recording paper unsuitable for the recording of the biological information of the patient can be quickly suppressed.

In the method for performing printing to a recording paper with a medical apparatus of the invention, detection of the first identification image may be performed on one surface of the recording paper, and printing of the biological information may not be performed in a case where the first identification image is not detected.

Since the detection of the first identification image is performed on one surface of the recording paper, for example, in a case where the surface of recording paper to which the first identification image is not attached is read (detected) (in a case where the front and back of the recording paper is not correctly mounted), the first identification image is not detected, and the printing of the biological information is not performed. In a case where the first identification image cannot be detected, the biological information of the patient is not printed on the recording paper. Thus, printing is not started. Accordingly, a user can be made to be aware of an abnormality, such as a mounting direction of the recording paper to the medical apparatus being in the opposite direction.

In addition, in the recording paper used for this printing method, the second identification image may be attached to the same surface as the first identification image or may be attached to a surface opposite to the first identification image. In a case where the second identification image is attached to the opposite surface, means for reading the second identification image may be located opposite to means for reading the first identification image.

In the method for performing printing on a recording paper with a medical apparatus of the invention, the expiration date information included in the information based on the second identification image may be marked with invisible ink visually unrecognizable with user's naked eyes, and may be encoded. The encoded expiration date information may be decoded using decoding information included in the information based on the first identification image.

In a case where the expiration date information is marked to the recording paper in a state in which the information can be visually recognized by a user, it is easy for a third party to manufacture a counterfeit product of this recording paper. As a result, the damage resulting from the expansion of crude counterfeit products from which printed letters are easily lost is increased. In contrast, in the invention, the second identification image, including the expiration date information, is marked with the invisible ink. Thus, counterfeiting or forgery of the recording paper can be prevented.

However, even in a case where the expiration date information is marked with the invisible ink that cannot be visually recognized by a user, it is not impossible to manufacture a counterfeit product by floating the invisible ink. Therefore, the counterfeit product damage cannot be reliably excluded.

In contrast, in the invention, even in a case where a counterfeit product with the same second identification image is manufactured, the counterfeit product cannot be used for the medical apparatus only with that. Accordingly, the counterfeit product damage can be suppressed.

In the method for performing printing on a recording paper with a medical apparatus of the invention, in the first identification image, a plurality of sensors lined up in a direction orthogonal to a feed direction of the recording paper in the medical apparatus may read different parts of the first identification image, respectively, and the recording paper may be determined to be the genuine product when at least one of the parts of the first identification image read by the plurality of sensors, respectively, coincides with the previously stored paper information.

For example, in the case of a configuration in which a portion of the first identification image is read in one sensor, even in a case where the recording paper has slightly meandered, a part different from a part that coincides with the stored paper information is read and compared. Accordingly, in this case, irrespective of being a genuine product, there is a possibility that this product may be determined not to be a genuine product.

In contrast, in the invention, different parts of the first identification image are read by the plurality of sensors, respectively, even in a case where the recording paper has slightly meandered, a part that coincides with the paper information stored by one of the sensors can be read. For this reason, when the recording paper mounted on the medical apparatus is fed, even in a case where the recording paper has slightly meandered, determination of a genuine product can be correctly executed.

A recording paper used for a medical apparatus of the invention is a recording paper on which acquired biological information of a patient is continuously printed. The recording paper includes a visually recognizable first identification image used for determination of whether or not the recording paper is a genuine product, and a second identification image used for determination of whether or not the recording paper is within the expiration date. In this case, a recording paper with no proper first identification image and second identification image can be prevented from being used for medical apparatus.

In the recording paper used for the medical apparatus of the invention, the second identification image may be located behind the first identification image in the feed direction. In this case, determination of a genuine product based on the first identification image can be first performed while feeding the recording paper, and reading of the second identification image becomes unnecessary in a case where the recording paper is determined not to be a genuine product.

In the recording paper used for the medical apparatus of the invention, the first identification image may be marked to one surface of the recording paper. In this case, the front and back of the recording paper can be determined depending on the presence/absence of the first identification image.

In the recording paper used for the medical apparatus of the invention, the expiration date information included in the information based on the second identification image may be marked with invisible ink visually unrecognizable with user's naked eyes, and may be encoded. The information based on the first identification image may include decoding information for decoding the encoded expiration date information. In this case, since duplication of the second identification image marked with the invisible ink is difficult, manufacturing of a counterfeit product can be prevented.

Advantageous Effects of Invention

According to the invention, loss of the biological information of a patient printed by the medical apparatus, or the like can be suppressed.

DESCRIPTION OF EMBODIMENTS

Hereinafter, an embodiment of a recording paper used for a medical apparatus related to the invention and a method for performing printing on the recording paper by the medical apparatus will be described referring to the drawings. In the following embodiment, a fetal and maternal monitor 1 is illustrated as the medical apparatus.

[Outline of Fetal and Maternal Monitor]

Figure 1:
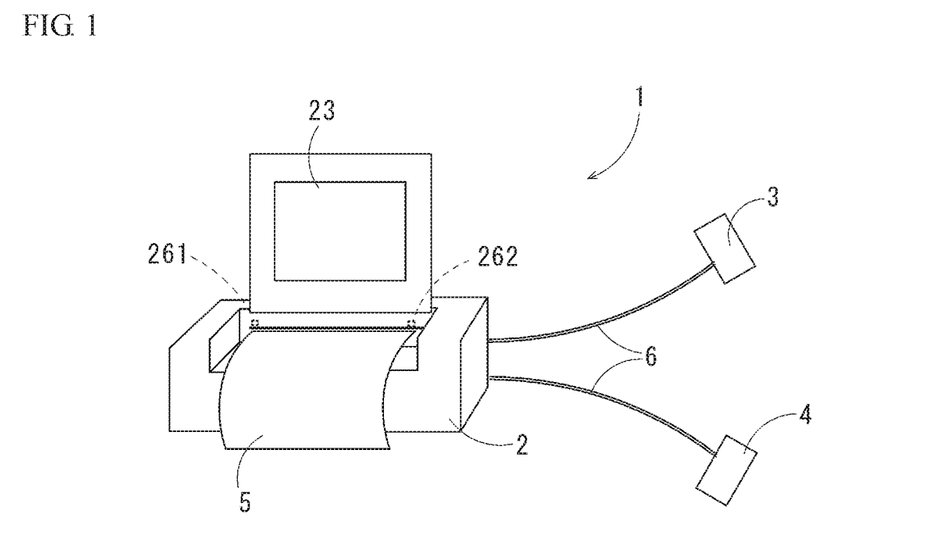
FIG. 1 is a schematic view illustrating a fetal and maternal monitor (medical apparatus) and recording paper related to an embodiment of the invention.

In the present embodiment, the fetal and maternal monitor 1, as illustrated in FIG. 1, includes a main body 2, an ultrasonic transducer 3, and a labor pain transducer 4. The main body 2 and the respective transducers 3 and 4 are electrically connected to each other by cables 6, respectively.

The ultrasonic transducer 3 outputs ultrasonic waves toward a fetus (a fetal heart) who is within a mother's body, and receives reflected waves of the ultrasonic waves, and transmits signals (hereinafter referred to as heartbeat signals) based on the reflected waves to the main body 2 via the cable 6. Additionally, the labor pain transducer 4 detects changes (the uterine muscle hardness of a maternal abdominal surface, or the like) in an abdominal wall due to uterine contraction, and transmits signals (hereinafter referred to as labor pain intensity signals) relating to the changes in the abdominal wall to the main body 2 via the cable 6.

The main body 2 receives the heartbeat signals output from the ultrasonic transducer 3 and the labor pain intensity signals output from the labor pain transducer 4, calculates the heart rate (fetal heart rate) and the labor pain intensity of the fetus who is within the mother's body, displays these on a display unit 23, and prints the fetal heart rate and the labor pain intensity on recording paper 5 loaded on the main body 2.

The fetal and maternal monitor 1 has features in the recording paper 5 used for the fetal and maternal monitor 1, and a method for printing the fetal heart rate and the labor pain intensity on the recording paper 5.

[Configuration of Recording Paper]

Figure 2:
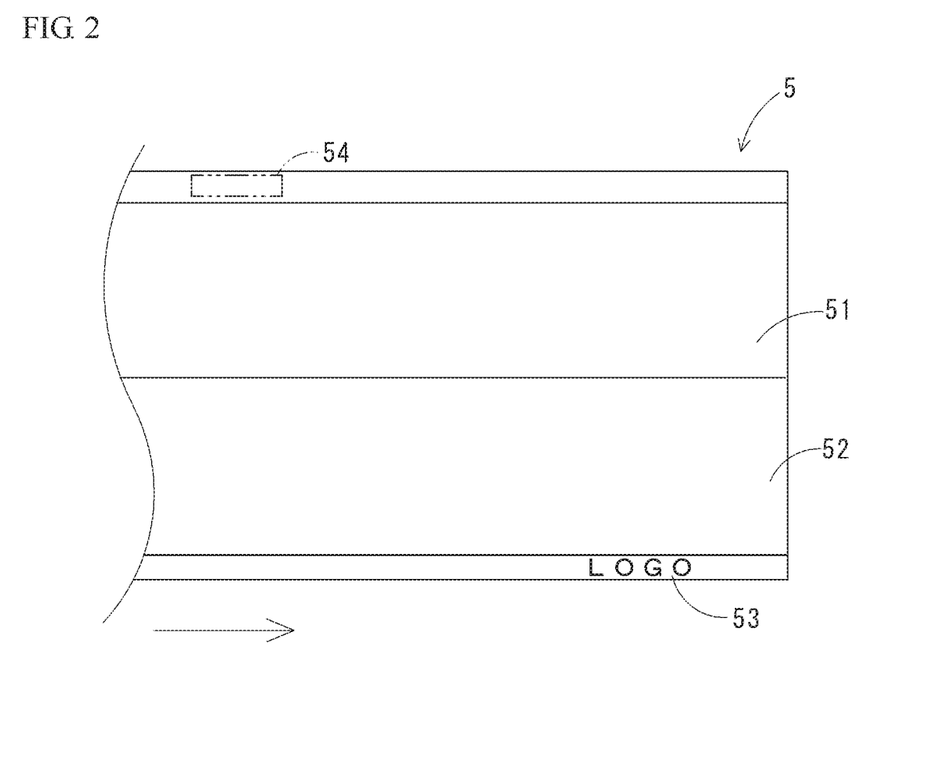
FIG. 2 is a schematic view illustrating a portion of the recording paper related to the above embodiment.

FIG. 2 is a schematic view illustrating a portion of the recording paper 5 in an enlarged manner. The recording paper 5 is constituted of thermal paper discolored by being heated, and is continuously folded in a band shape. A feed direction of the recording paper 5 by the fetal and maternal monitor 1 is indicated by an arrow in FIG. 2. As illustrated in FIG. 2, the recording paper 5 has a single side (one surface) as a printing surface, and the printing surface is provided with a first region 51 where the fetal heart rate is printed, a second region 52 where the labor pain intensity is printed, a first identification image 53, and a second identification image 54.

The first region 51 and the second region 52 are formed at positions excluding both side parts of the recording paper 5. The first region 51 is located on a right side (an upper side of FIG. 2) as seen from a front side in the feed direction of the recording paper 5 in the printing surface of the recording paper 5. The second region 52 is located on a left side (a lower side of FIG. 2) of the first region 52.

The first identification image 53 is located on the printing surface on the leftmost side, that is, on the left side (a left side part of the recording paper 5, the lower side in FIG. 2) of the second region 52 as seen from the front side in the feed direction, out of both side parts of the recording paper 5. Additionally, the dimension of the first identification image 53 in a direction orthogonal to the feed direction is set to such a dimension that the entirety of the image 53 can be scanned by a plurality of (three in the present embodiment) sensors 261A to 261C (refer to FIG. 4) that constitute a first sensor unit 261 to be described below.

The first identification image 53 is constituted by, for example, a registered trademark that has undergone trademark registration, and is attached to the printing surface of the recording paper 5 in a state (for example, black printing)

where a user can recognize the registered trademark. Information (hereinafter referred to as first identification information) based on the first identification image 53 is used for determination of whether or not the recording paper 5 is an exclusive article (hereinafter referred to as a genuine product) manufactured so as to be used by the fetal and maternal monitor 1. Additionally, the first identification image 53 includes decoding information for acquiring expiration date information included in a state where encoding into information (hereinafter, second identification information) based on the second identification image 54 is performed.

In addition, the first identification image 53 is constituted by the registered trademark but is not limited thereto, and may have any shapes as long as the first identification image is displayed in a state where the user can visually recognize the first identification image. As the first identification image 53 that can be visually recognized is provided on a single side of the recording paper 5, the user can check the front and back when the recording paper 5 is loaded on the fetal and maternal monitor 1.

The second identification image 54 is located on the rightmost side, that is, on the right side (a right side part of the recording paper 5, the upper side in FIG. 2) of the first region 51 as seen from the front side in the feed direction, out of both the side parts of the recording paper 5. The second identification image 54 is attached to the printing surface of the recording paper 5 in a state (for example, colorless printing) where the user cannot visually recognize the second identification image. Specifically, the second identification image 54 is an identification image marked with invisible ink or the like that cannot be visually recognized with user's naked eyes. The second identification image 54 is constituted by, for example, barcodes, and includes expiration date information (manufacturing date, lot number, or warranty date) of the recording paper 5 in an encoded state.

The second identification image 54 is located behind the first identification image 53 in the feed direction of the recording paper 5. That is, the first identification image 53 and the second identification image 54 are disposed to face each other with the first region 51 and the second region 52 interposed therebetween, and the first identification image 53 is located on the front side in the feed direction.

In the present embodiment, the second identification image 54 is attached to the recording paper 5 with the invisible ink that cannot be visually recognized by the user. However, the invention is not limited to this. For example, the second identification image 54 may be attached in a state where the image can be identified by the user similarly to the first identification image 53. Additionally, the second identification image 54 may be located in front of the first identification image 53 in the feed direction. Moreover, the second identification image 54 may be located along with the left side part of the recording paper 5 similarly to the first identification image 53, or the first identification image 53 may be located along with the right side part of the recording paper 5 similarly to the second identification image 54. In addition, the first identification image 53 and the second identification image 54 are not limited to one each and may be plural at predetermined intervals over the entire length of the recording paper 5.

[Configuration of Main Body]

Figure 3:
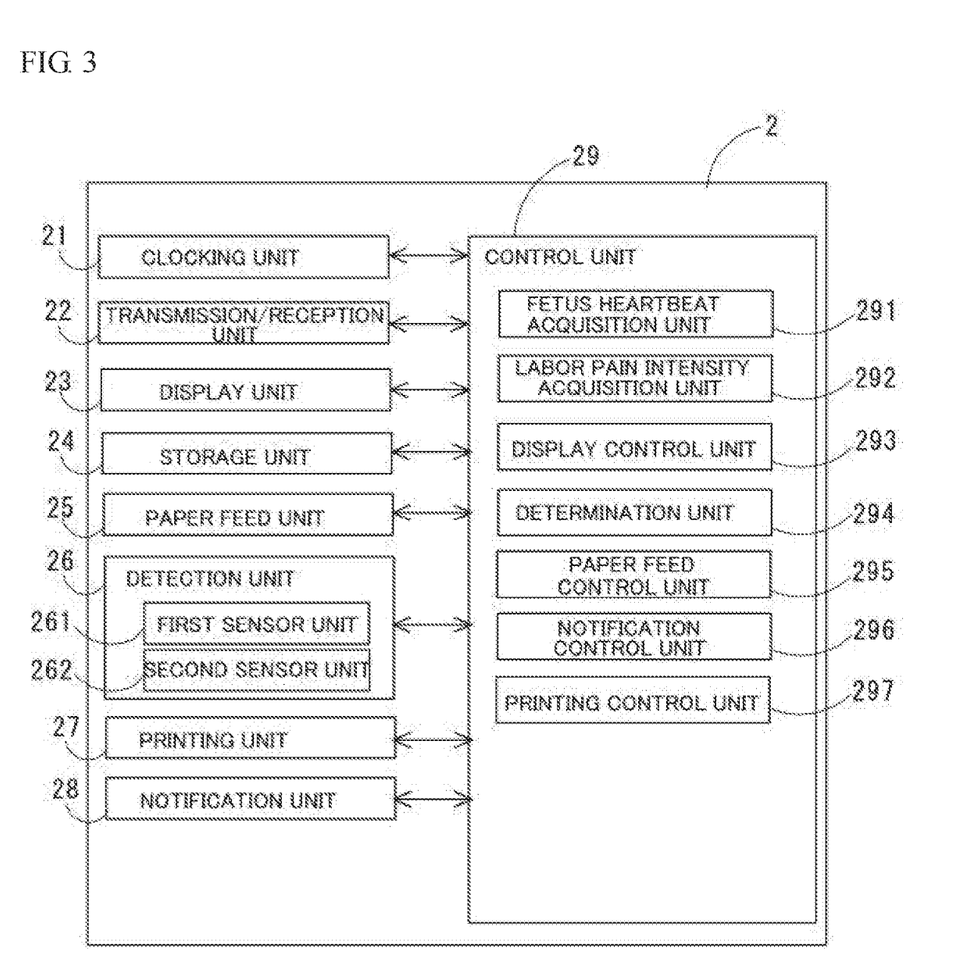
FIG. 3 is a block diagram illustrating the configuration of a main body of the fetal and maternal monitor related to the above embodiment.

As illustrated in FIG. 3, the main body 2 includes a clocking unit 21, a transmission/reception unit 22, a display unit 23, a storage unit 24, a paper feed unit 25, a detection unit 26, a printing unit 27, a notification unit 28, and a control unit 29 that controls the respective units 21 to 28.

[Configuration of Clocking Unit]

The clocking unit 21 clocks the current date and time.

[Configuration of Transmission/Reception Unit]

The transmission/reception unit 22 transmits drive signals or the like to the ultrasonic transducer 3 and the labor pain transducer 4 in addition to receiving the heartbeat signals from the ultrasonic transducer 3 connected to the main body 2 via the cable 6 and the labor pain intensity signals from the labor pain transducer 4.

[Configuration of Display Unit]

The display unit 23 displays the fetal heart rate acquired by performing calculation by a fetus heartbeat acquisition unit 291 in the control unit 29 and the labor pain intensity acquired by performing calculation by a labor pain intensity acquisition unit 292 in the control unit 29, from the heartbeat signals and the labor pain intensity signals received by the transmission/reception unit 22.

Either the fetal heart rate or the labor pain intensity may be displayed on the display unit 23. In addition to these, an average value of the fetal heart rate, or the like, may be displayed. Additionally, a display providing a notification that the mounting direction (front and back) of the recording paper 5 is reversed, a display providing a notification that the recording paper 5 is not a genuine product, a display notifying that the expiration date of the recording paper 5 has passed, and the like may be performed on the display unit 23.

[Configuration of Storage Unit]

The storage unit 24 records the fetal heart rate, the labor pain intensity in association with the current date and time clocked by the clocking unit 21. The storage unit 24 stores various programs related to the driving of the main body 2 in addition to the fetal heart rate and the labor pain intensity. Additionally, paper information for determining whether or not the first identification image 53 detected by the first sensor unit 261 to be described below is an identification image attached to the genuine product is previously stored in the storage unit 24.

[Configuration of Paper Feed Unit]

The paper feed unit 25 supplies the recording paper 5 mounted on the main body 2 to the printing unit 27, and discharges the printing paper to the outside of the main body 2 after the printing. The paper feed unit 25 is constituted by, for example, rollers that respectively abut against a front surface (printing surface) and a back surface of the recording paper 5, a motor that rotates the rollers, and the like.

[Configuration of Detection Unit]

The detection unit 26 includes the first sensor unit 261 and the second sensor unit 262. As illustrated in FIG. 1, the first sensor unit 261 is disposed to face a position through which the first identification image 53 (left side part of the recording paper 5) of the recording paper 5 passes, and detects the first identification image 53 of the recording paper 5. Specifically, the first sensor unit 261 is constituted by a plurality of sensors (three sensors 261A to 261C) that are lined up in the direction orthogonal to the feed direction of the recording paper 5. As illustrated at an upper part of FIG. 4, each of the individual sensors 261A to 261C performs scanning above of the first identification image 53 in the feed direction as the recording paper 5 is fed by the paper feed unit 25. Accordingly, the individual sensors 261A to 261C detect different parts (individual images at positions illustrated by one-dot chain lines of FIG. 4) of the first identification image 53.

Figure 4:
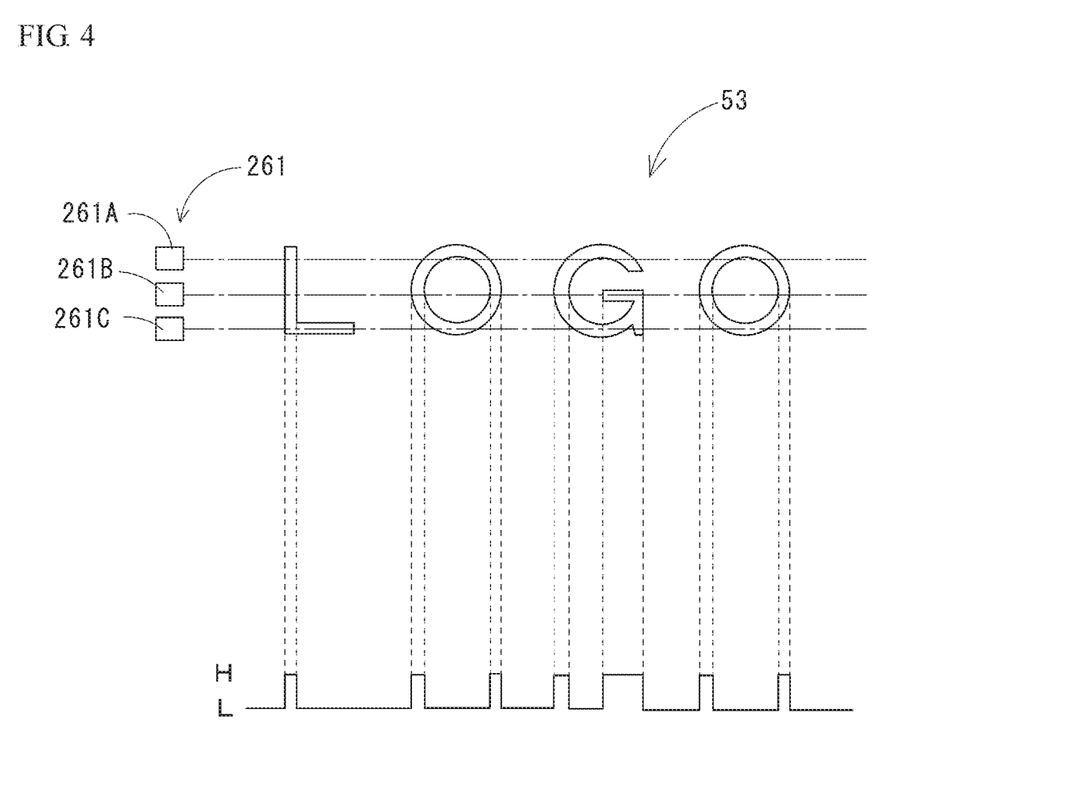
FIG. 4 is a view illustrating a first identification image and a first sensor unit related to the above embodiment, and examples of output signals to be output from the first sensor unit.

For example, a case where a LOGO mark illustrated at the upper part of FIG. 4 is detected as the first identification image 53 will be described. Since each of the sensors 261A to 261C outputs "H" when a text portion (black background portion) has been detected and outputs "L" when the other portion (white background portion) has been detected, for example, the output from the sensor 261B at the center in a width direction becomes signals illustrated at a lower part of FIG. 4. In this way, the first identification information (information at a plurality of spots lined up in the direction orthogonal to the feed direction in the first identification image 53) based on the first identification image 53 is acquired by the first sensor unit 261.

In addition, in the present embodiment, the first sensor unit 261 is constituted by the three sensors 261A to 261C. However, the first sensor unit is not limited to this and may be constituted one or two sensors or may be constituted by four or more sensors.

As illustrated in FIG. 1, the second sensor unit 262 is disposed to face a position through which the second identification image 54 (right side part of the recording paper 5) of the recording paper 5 passes, and detects the second identification image 54 of the recording paper 5. Specifically, the second sensor unit 262 detects the second identification image 54, for example, by projecting light of a predetermined wavelength onto the second identification image 54 marked with the invisible ink to detect the reflected light thereof. Information, including the manufacturing date, lot number, or warranty date of the recording paper 5 included in the second identification information based on the second identification image 54 is encoded and is acquired using the decoding information included in the first identification information based on the first identification image 53.

In addition, in the present embodiment, the second identification image 54 is detected as a sensor that constitutes the second sensor unit 261 detects the projected light of the predetermined wavelength. However, the invention is not limited to this, and methods for detecting the second identification image 54 are appropriately changed in accordance with the characteristics of the invisible ink that forms the second identification image 54.

[Configuration of Printing Unit]

The printing unit 27 is constituted by, for example, a thermal head or the like, and sequentially prints the fetal heart rate continuously acquired by the labor pain intensity acquisition unit 292, on the first region 51 of the recording paper 5 and the labor pain intensity continuously acquired by the labor pain intensity acquisition unit 292, on the second region 52.

[Configuration of Notification Unit]

In a case where printing of the fetal heart rate and the labor pain intensity to the recording paper 5 is not possible, the notification unit 28 is constituted by, for example, a buzzer, a red lamp, or the like notifies the user of the fact using sound output in the buzzer, ON/OFF of the red lamp, or the like.

In addition, as well as the notification unit 28 constituted by the buzzer, the red lamp, or the like, for example, the display unit 23 may display that printing to the recording paper 5 is not possible, and the display in the display unit 23 may be performed in addition to the notification by the notification unit 28.

[Configuration of Control Unit]

The control unit 29 controls the clocking unit 21, the transmission/reception unit 22, the display unit 23, the storage unit 24, the paper feed unit 25, the detection unit 26, the printing unit 27, and the notification unit 28, which are described above. The control unit 29 functions as the fetus heartbeat acquisition unit 291, the labor pain intensity acquisition unit 292, a display control unit 293, a determination unit 294, a paper feed control unit 295, a notification control unit 296, and a printing control unit 297.

The fetus heartbeat acquisition unit 291 calculates and acquires the fetal heart rate on the basis of the heartbeat signals acquired by the transmission/reception unit 22 from the ultrasonic transducer 3.

The labor pain intensity acquisition unit 292 calculates and acquires labor pain intensity from the labor pain transducer 4 on the basis of the labor pain intensity signals acquired by the transmission/reception unit 22.

The fetal heart rate acquired by the fetus heartbeat acquisition unit 291 and the labor pain intensity acquired by the labor pain intensity acquisition unit 292 are associated with the date and time when the ultrasonic transducer 3 and the labor pain transducer 4 have detected the heartbeat signals and the labor pain intensity signals, and are recorded on the storage unit 24.

The display control unit 293 displays the fetal heart rate acquired by the fetus heartbeat acquisition unit 291 and the labor pain intensity acquired by the labor pain intensity acquisition unit 292 on the display unit 23. Additionally, on the basis of determination results of the determination unit 294 to be described below, the display control unit 293 may make the display unit 23 display that the mounting state of the recording paper 5 is not correct, the recording paper 5 is not a genuine product, the expiration date of the recording paper 5 passes, and the like.

The determination unit 294 determines whether or not the recording paper 5 is a genuine product. Specifically, the determination unit 294 determines whether or not the recording paper 5 is a genuine product, on the basis of the result of whether or not the first identification information based on the first identification image 53 detected by the first sensor unit 261 of the detection unit 26, and the paper information previously stored in the storage unit 24 coincide with each other.

Additionally, the determination unit 294 determines whether the recording paper 5 is within the expiration date. Specifically, the determination unit 294 determines whether or not the second identification image 54 has been acquired by the second sensor unit 262 of the detection unit 26, and in a case where it is determined that the second identification image 54 has been acquired, the determination unit 294 decodes the encoded information included in the second identification information based on the second identification image, using the decoding information included in the first identification information based on the first identification image 53, compares the acquired warranty date (expiration date) of the recording paper 5 with the current date and time clocked by the clocking unit 21, and determines whether or not the recording paper 5 is within the expiration date.

In addition, in a case where the lot number or the manufacturing date is attached as the encoded information, whether or not the recording paper 5 is within the expiration date can be determined if the warranty date (expiration date) for each lot number or manufacturing date is previously stored in association in the storage unit 24.

Moreover, the determination unit 294 determines whether or not the fetal heart rate is being acquired by the fetus heartbeat acquisition unit 291 and the labor pain intensity is being acquired by the labor pain intensity acquisition unit 292, in addition to determining whether or not a predetermined amount of biological information (the fetal heart rate and the labor pain intensity) acquired by the fetus heartbeat acquisition unit 291 and the labor pain intensity acquisition unit 292 is recorded in the storage unit 24.

The paper feed control unit 295 controls the paper feed unit 25 on the basis of the determination results of the determination unit 294, or the like, and makes the paper feed unit 25 perform supply or stop of the recording paper 5 at a normal speed or a high speed.

The notification control unit 296 controls the notification unit 28 on the basis of the determination results of the determination unit 294, and makes the notification unit 28 perform a notification that the fetal heart rate and the labor pain intensity are not printed on the recording paper 5. In this case, the display control unit 293 may make the display unit 23 display that the printing is not performed.

The printing control unit 297 controls the printing unit 27 on the basis of the determination results of the determination unit 294. Specifically, the printing control unit 297 drives the printing unit 27 to print the fetal heart rate and the labor pain intensity only in a case where it is determined in the determination results of the determination unit 294 that the recording paper 5 is a genuine product and the recording paper 5 is within the expiration date.

The printing control unit 297 makes the printing unit 296 print the fetal heart rate and the labor pain intensity (biological information), which are acquired until the determination by the determination unit 294 is executed and are recorded (stored) in the storage unit 24 at a high speed, and then, print the fetal heart rate and the labor pain intensity substantially simultaneously with the acquisition.

[Printing Processing to Recording Paper]

Figure 5:
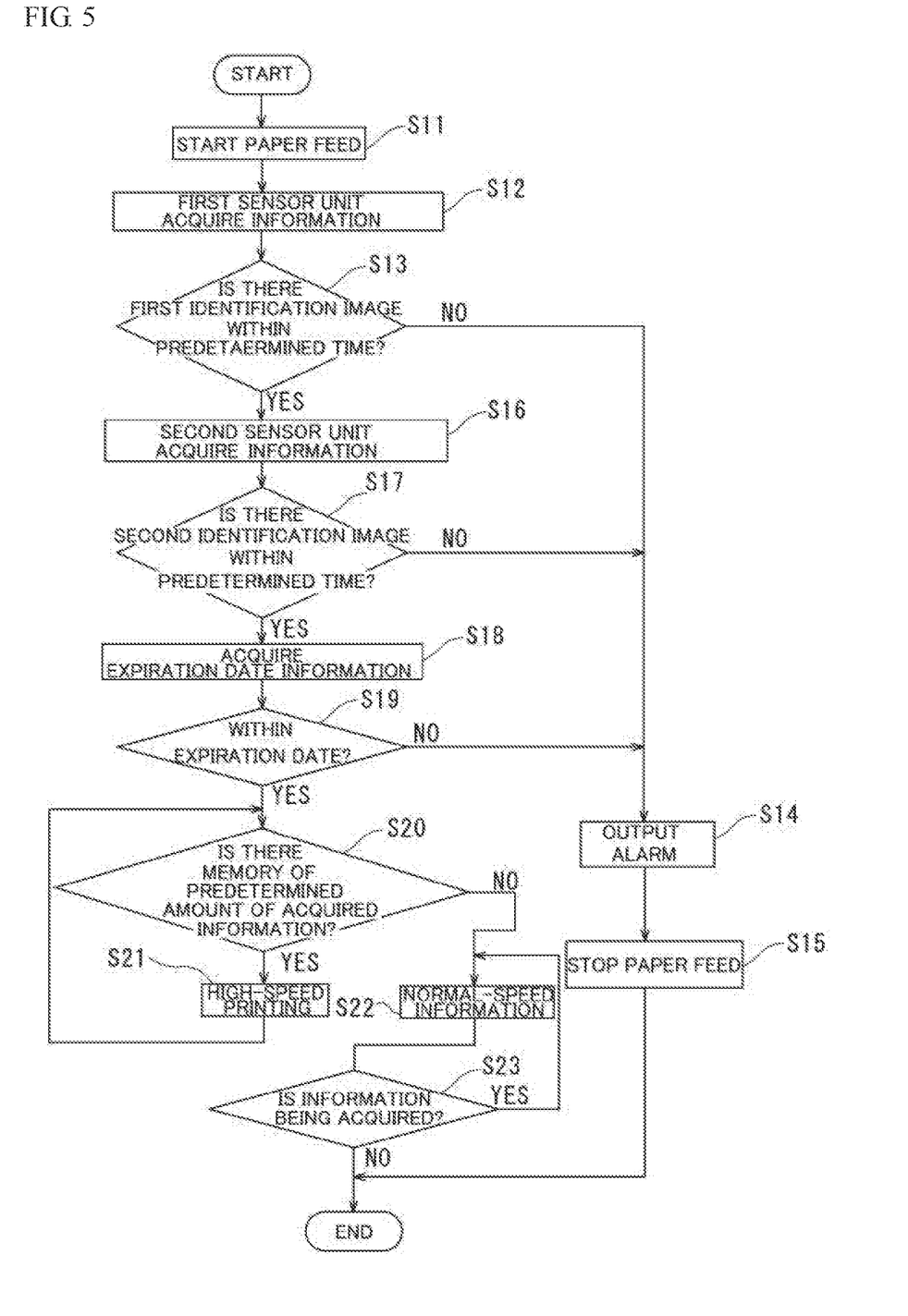
FIG. 5 is a flowchart illustrating printing processing to be executed by the fetal and maternal monitor related to the above embodiment.

FIG. 5 is a flowchart illustrating the printing processing to be executed by the control unit 29. The control unit 29 executes the printing processing to the recording paper 5 in accordance with a procedure illustrated in FIG. 5.

First, the recording paper 5 is mounted on the main body 2, the paper feed control unit 295 drives the paper feed unit 25 to start the paper feed of the recording paper 5 (Step S11). If the paper feed of the recording paper 5 is started by this Step S11, the first sensor unit 261 continuously scans the left side part of the recording paper 5 to acquire the first identification image 53 (the first identification information) (Step S12).

Then, the determination unit 294 determines whether or not the recording paper 5 is a genuine product on the basis of the result of whether or not the first identification information based on the first identification image 53 acquired by the first sensor unit 261 and the paper information previously stored in the storage unit 24 coincide with each other (Step S13).

In a case where the first identification image is not acquired by the first sensor unit 261 while the paper feed is performed by a predetermined amount or in a case where the acquired first identification information and the paper information previously stored in the storage unit 24 do not coincide with each other, that is, in a case where the recording paper 5 is not correctly mounted on the main body 2 such that the mounting direction of the recording paper 5 is turned upside down or in a case where the regular first identification image 53 is not attached to a predetermined position of the recording paper 5 because the mounted recording paper 5 is not a genuine product, the determination unit 294 determines to be "NO" in determination processing of Step S13. In addition, the determination unit 294 determines that the recording paper 5 is a genuine product when at least one of the parts of the first identification image 53 that are respectively read by the plurality of sensors 261A to 261C that constitute the first sensor unit 261 coincides with the paper information previously stored in the storage unit 24.

If "NO" is determined in the determination processing of Step S13, the notification control unit 295 controls the notification unit 28 to output an alarm (Step S14). Simultaneously, the paper feed control unit 295 controls the paper feed unit 25 to stop the paper feed of the recording paper 5 (Step S15), and terminates the printing processing.

On the other hand, if "YES" is determined in the determination processing of Step S13, the second sensor unit 262 continuously scans a region above the first region 51 of the recording paper 5 to acquire the second identification image (second identification information) (Step S16).

Then, the determination unit 294 determines whether or not the second identification image 54 has been acquired by the second sensor unit 262, similarly to the acquisition determination of the first identification image 53 (Step S17). In a case where the information acquired by the second sensor unit 262 is not the second identification image 54 or in a case where the second identification image 54 cannot be acquired even if a predetermined time passes after the detection of the first identification image 53, the determination unit 294 determines to be "NO" in the determination processing of Step S17.

If "NO" is determined in the determination processing of Step S17, similarly to the case where "NO" is determined in the above Step S13, the notification control unit 295 controls the notification unit 28 to output an alarm (Step S14), and the paper feed control unit 295 controls the paper feed unit 25 to stop the paper feed of the recording paper 5 (Step S15), and terminates the printing processing.

On the other hand, if "YES" is determined in the determination processing of Step S17, the determination unit 294 encodes the encoded information included in the second identification information, using the decoding information included in the first identification information based on the first identification image 53, and acquires the expiration date information, such as the warranty date of the recording paper 5 (Step S18).

Then, the warranty date of the recording paper 5 acquired by Step S18 is compared with the current date and time clocked by the clocking unit 21, and whether or not the recording paper 5 is within the expiration date is determined (Step S19).

If "NO" is determined in the determination processing of Step S19, similarly to the case where "NO" is determined in the above Step S13 and Step S17, the notification control unit 295 controls the notification unit 28 to output an alarm (Step S14), and the paper feed control unit 295 controls the paper feed unit 25 to stop the paper feed of the recording paper 5 (Step S15), and terminates the printing processing.

On the other hand, if "YES" is determined in the determination processing of Step S19, the determination unit 294 determines whether or not the recording of the biological information (the fetal heart rate and the labor pain intensity) acquired by the fetus heartbeat acquisition unit 291 and the labor pain intensity acquisition unit 292 are stored by predetermined amounts or more in the storage unit 24 (for example, whether or not the acquired recording is stored without being printed for several seconds or more) (Step S20).

If "YES" is determined in the determination processing of Step S20, the printing control unit 295 drives the printing unit 27, and the paper feed control unit 295 controls the paper feed unit 25 to print the recording of the fetal heart rate and the labor pain intensity, which are respectively stored in the storage unit 24, in the first region 51 and the second region 52 at a high speed (start the printing) (Step S21).

On the other hand, if "NO" is determined in the determination processing of Step S20, the printing control unit 295 drives the printing unit 27 to print the fetal heart rate and the labor pain intensity at a normal speed substantially simultaneously with the acquisition on the first region 51 and the second region 52 (to start the printing) (Step S22). In addition, in a case where printing is started simultaneously with the acquisition of the biological information, or in a state where there is little recording storage of the acquired information on the fetal heart rate and the labor pain intensity to the storage unit 24 such as after printing equivalent to the recording storage is performed by high-speed printing, a state where printing is performed substantially simultaneously with the acquisition of the information continues. However, in a case where the recording storage of the acquired information is present even at a predetermined amount or less, the acquired information stored before new acquisition information is sequentially printed while the new acquisition information is first stored. Thus, the printing is performed after a slight time lag from the information acquisition.

Then, if the printing of the fetal heart rate and the labor pain intensity at the normal speed is started, the determination unit 294 determines whether or not the fetal heart rate and the labor pain intensity are being acquired by the fetus heartbeat acquisition unit 291 and the labor pain intensity acquisition unit 292 (the presence/absence of reception of the heartbeat signals from the ultrasonic transducer 3 and reception of the labor pain intensity signals from the labor pain transducer 4) (Step S23).

The printing of the fetal heart rate and the labor pain intensity by the printing unit 27 is continued until the heartbeat signals and the labor pain intensity signals are no longer received from the ultrasonic transducer 3 and the labor pain transducer 4, that is, until the fetal heart rate and the labor pain intensity are no longer acquired by the fetus heartbeat acquisition unit 291 and the labor pain intensity acquisition unit 292 ("NO" in Step S23).

The printing processing is ended if the fetal heart rate (heartbeat signals) and the labor pain intensity (labor pain intensity signals) are no longer acquired ("YES" in Step S23). In this case, the acquisition (the recording in the storage unit 24) of the biological information may be ended simultaneously with the end of the printing processing.

According to this fetal and maternal monitor (medical apparatus) 1, for example, in a case where the recording paper 5 is not a genuine product, in a case where the expiration date passes, in a case where the recording paper 5 is correctly mounted, or the like, the fetal heart rate and the labor pain intensity (biological information) are not printed on the recording paper 5. Thus, use of low-quality recording paper with a possibility that printed letters may be lost within a predetermined period (before expiration of a legal storage period) or yellowing or blurring may occur can be prevented, a recording mistake resulting from erroneous mounting of the recording paper 5 can also be prevented, and loss of storage information, such as the fetal heart rate and the labor pain intensity can be prevented.

Additionally, for example, in a case where a user has mounted a counterfeit product, the recording paper 5, of which the expiration date has passed, or the like, on the fetal and maternal monitor 1, the fetal heart rate and the labor pain intensity are not printed on the recording paper 5 that is not proper. Accordingly, the user can be urged to use a genuine product within an expiration date.

Moreover, by using a logo mark with which a manufacturing company or a sales company for the recording paper 5, a manufacturing company or a sales company for the fetal and maternal monitor 1 has received trademark registration as the first identification image 53, manufacturing of the recording paper 5 with the first identification image 53 by those other than a trademark owner can be suppressed, and counterfeit product damage can be further suppressed. (In addition, since the labor pain intensity and the fetal heart rate of a mother's body are recorded on the genuine product within the expiration date, it is possible to suppress that these kinds of information is lost before elapse of legal storage life).

Since the first identification image 53 used for the determination processing of a genuine product is located in front of the second identification image 54 in the feed direction of the recording paper 5, the determination processing of the genuine product can be first performed. For this reason, in a case where the recording paper 5 is determined not to be a genuine product, it is not necessary to execute the determination processing based on the second identification image. Thus, printing to unsuitable recording paper can be quickly suppressed without performing reading of the second identification image 54. Additionally, since the first identification image 53 that can be visually recognized is attached only to a single side (printing surface) of the recording paper 5, it is easy to check the front and back of the recording paper 5. Moreover, even in a case where the recording paper 5 is mounted on the fetal and maternal monitor 1 with the front and back thereof inverted, the fetal heart rate and the labor pain intensity is not printed on the recording paper 5. Accordingly, it is possible to recognize that the mounting direction of the recording paper 5 is not correct.

In the present embodiment, since the expiration date information included in the second identification information based on the second identification image 54 is marked with invisible ink and encoded, a counterfeit product imitating only a visible portion cannot be used by the fetal and maternal monitor 1. Accordingly, the counterfeit product damage can be more effectively prevented.

In the present embodiment, when any part of the first identification image 53 detected by each of the plurality of sensors 261A to 261C that constitute the first sensor unit 261 coincides with the previously stored paper information, the recording paper 5 is determined to be a genuine product. Thus, for example, even in a case where the recording paper 5 mounted on the fetal and maternal monitor 1 (main body 2) has slightly meandered during paper feed, the determination of whether or not the recording paper 5 is a genuine product can be more reliably executed.

In addition, the invention is not limited to the above embodiment, and various changes can be made without departing the spirit of the invention.

In the above embodiment, as long as the first identification information and the paper information do not completely coincide with each other even if these kinds of information coincide with each other within a preset range, the recording paper is determined to be a genuine product. However, whether or not the entire first identification image detected by the first sensor unit coincides with the paper information previously stored in the storage unit may be determined.

Additionally, in the determination processing of Step S23, the printing processing is continued until the fetal heart rate and labor pain intensity are no longer acquired by the fetus heartbeat acquisition unit 291 and the labor pain intensity acquisition unit 292, and the printing processing is ended if the fetal heart rate and labor pain intensity are no longer acquired. However, the invention is not limited to this, and the printing processing may be ended if printing is performed for a predetermined time (for example, for 40 minutes).

Additionally, in the determination processing of Step S20, whether or not a predetermined amount of the acquired information (the fetal heart rate and the labor pain intensity) is recorded in the storage unit 24, and the printing speed of the fetal heart rate and the labor pain intensity is changed in accordance with the result. However, the invention is not limited to this, and the determination processing of Step S20 may not be performed. In this case, in a case where "YES" is determined in determination processing of S19, the printing processing is started at a normal speed while recording the acquired fetal heart rate and labor pain intensity, the printing may be sequentially performed at the normal speed from the fetal heart rate and the labor pain intensity that are recorded and stored before the start of the printing, or the printing may be sequentially performed at the normal speed while acquiring the heart rate and the labor pain intensity after the start of the printing without printing the fetal heart rate and the labor pain intensity that are recorded and stored in the storage unit 24.

In the above embodiment, the determination processing of Step S13 of determining whether or not the first identification image 53 has been acquired within a predetermined time, and the determination processing of Step S17 of determining whether or not the second identification image 54 has been acquired within the predetermined time are executed once, respectively, after the paper feed is started. However, the invention is not limited to this. For example, a plurality of the first identification images 53 and the second identification images 54 are attached at predetermined intervals over the entire length of the recording paper 5, and the processing of the above Steps S12 to S19 may be executed every time a predetermined amount of the recording paper 5 is fed even after high-speed printing or normal printing is started.

According to this, in a case where a counterfeit product to which a genuine product equivalent to one page (a length including one first identification image 53 and one second identification image 54) is connected to a first page is used, the printing processing for the counterfeit product can be stopped. That is, the processing of the above Steps S12 to S19 is executed every time a predetermined amount of the recording paper 5 is fed. Thus, even if the printing is started in the portion of the genuine product, in the portion of the counterfeit product after a predetermined time passes (that is, after a predetermined amount of the recording paper 5 is fed), a first identification image and a second identification image are not acquired, and the printing is stopped. Hence, use of the counterfeit product in which a portion of the genuine product as described portion has been used can be suppressed. Thus, a user can be strongly urged to use a genuine product within an expiration date, and information storage imperfection and the counterfeit product damage resulting from low-quality recording paper being used can be reliably suppressed.

In the above embodiment, a case where the fetal and maternal monitor 1 is exemplified as a medical apparatus, and the labor pain intensity and the fetal heart rate are printed as biological information has been described. However, the invention is not limited to the fetal and maternal monitor 1, and the invention can be applied to any medical apparatus as long as medical apparatus that record a patient's biological information are provided. For example, the invention can be applied to recording paper in medical apparatus that record biological information, such as SpO2 (arterial oxygen saturation), electrocardiograms, brain waves of patients, and a printing method therefor.

INDUSTRIAL APPLICABILITY

Information acquired in medical apparatus, such as the fetal and maternal monitor, can be reliably printed on the recording paper, and the recording paper can be kept while maintaining quality for a prolonged period of time.

What is claimed is:

1. A method for performing printing on a recording paper with a medical apparatus that continuously prints acquired biological information of a patient on the recording paper while feeding the recording paper, the method comprising:
   reading a first identification image attached to the recording paper, and determining whether or not the recording paper is a genuine product on the basis of a comparison result between information based on the read first identification image and paper information previously stored in the medical apparatus;
   reading a second identification image attached to the recording paper, and determining whether or not the recording paper is within an expiration date on the basis of expiration date information included in information based on the read second identification image; and
   printing the biological information on the recording paper in a case where the recording paper is determined to be the genuine product and the recording paper is determined to be within the expiration date, wherein
   the expiration date information included in the information based on the second identification image is marked with invisible ink visually unrecognizable with user's naked eyes, and is encoded, and
   the encoded expiration date information is decoded using decoding information included in the information based on the first identification image.

2. The method according to claim 1,
   wherein the second identification image is read only in a case where the recording paper is determined to be the genuine product by using the first identification image.

3. The method according to claim 1,
   wherein detection of the first identification image is performed on one surface of the recording paper, and printing of the biological information is not performed in a case where the first identification image is not detected.

4. The method according to claim 1,
   wherein in the first identification image, a plurality of sensors lined up in a direction orthogonal to a feed direction of the recording paper in the medical apparatus read different parts of the first identification image, respectively, and
   wherein the recording paper is determined to be the genuine product when at least one of the parts of the first identification image read by the plurality of sensors, respectively, coincides with the previously stored paper information.

5. A recording paper, used for a medical apparatus, on which acquired biological information of a patient is continuously printed, the recording paper comprising:
   a visually recognizable first identification image used for determination of whether or not the recording paper is a genuine product and
   a second identification image used for determination of whether or not the recording paper is within an expiration date, wherein expiration date information included in the second identification image is marked with invisible ink visually unrecognizable with user's naked eyes, and is encoded, and the first identification image includes decoding information for decoding the encoded expiration date information.

6. The recording paper according to claim 5, wherein the second identification image is located behind the first identification image in a feed direction of the recording paper.

7. The recording paper according to claim 5, wherein the first identification image is attached to one surface of the recording paper.

\* \* \* \* \*